United States Patent [19]

McEntire et al.

[11] 4,371,704
[45] Feb. 1, 1983

[54] SUBSTITUTED ALKYLENE OXIDES FROM SUBSTITUTED ALKYLENE CARBONATES

[75] Inventors: Edward E. McEntire; Robert M. Gipson, both of Austin, Tex.

[73] Assignee: Texaco Development Corporation, White Plains, N.Y.

[21] Appl. No.: 93,319

[22] Filed: Nov. 13, 1979

Related U.S. Application Data

[63] Continuation-in-part of Ser. No. 920,908, Jun. 29, 1978, abandoned.

[51] Int. Cl.$^3$ .......................................... C07D 317/36
[52] U.S. Cl. ............................................................ 549/518
[58] Field of Search ..................... 260/348.16; 549/518

[56] References Cited

U.S. PATENT DOCUMENTS 4,069,234 1/1978 Wu ................................ 260/348.16

FOREIGN PATENT DOCUMENTS 893037 5/1944 France ........................... 260/348.16

OTHER PUBLICATIONS

A. L. Shapiro et al., Jour. Org. Chem., USSR, (1969), vol. 5, No. 2, pp. 200–203.
E. D. Bergmann et al., Jour. Chem. Soc. (C), (1966), pp. 899–900.

Primary Examiner—Norma S. Milestone
Attorney, Agent, or Firm—Robert A. Kulason; Kenneth R. Priem; David L. Mossman

[57] ABSTRACT

Alkyl substituted ethylene carbonates are converted to substituted ethylene oxides by heating the respective carbonates in the presence of a catalyst which is selected from the group of alkali metal halides consisting of lithium fluoride, sodium fluoride, potassium fluoride, sodium chloride and potassium chloride. The alkyl substituted ethylene carbonates have the general formula

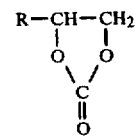

where R is alkyl, aryl, substituted alkyl, substituted aryl, alkaryl or aralkyl.

6 Claims, No Drawings

SUBSTITUTED ALKYLENE OXIDES FROM SUBSTITUTED ALKYLENE CARBONATES

This application is a continuation-in-part of application, Ser. No. 920,908 filed June 29, 1978, abandoned.

BACKGROUND OF THE INVENTION

1. Field of the Invention

This invention concerns the conversion of substituted ethylene carbonates into substituted ethylene oxide by catalytic pyrolysis.

2. Discussion of the Prior Art

Substituted ethylene oxides or epoxides are well known in the art as monomers in preparation of resins of various types ranging from epoxy adhesive applications to elastomeric solvent-resistant polymers for use in making tubing, shoe soles and the like. Such epoxides are also useful for the preparation of polyols for use in polyurethane products. These epoxides may be prepared by the direct oxidation of an olefin but such a process has failed due to the formation of large amounts of by-products and a very small amount of the desired epoxide. Other methods known in the art for producing substituted ethylene epoxides from substituted ethylene carbonates include the use of alkali metal carbonates as catalysts. This is disclosed in Offenlegungsschrift No. 1,940,205. Also U.S. Pat. No. 2,851,469 (1958) describes the pyrolysis of ethylene carbonate with polyhalogenated hydrocarbon catalysts.

When alkali metal carbonates are used as catalysts as above, high temperatures are required which lowers the selectivities somewhat. U.S. Pat. No. 2,851,469 above uses catalysts which are quite expensive.

A. L. Shapiro, S. Z. Levin and V. P. Chekhovskaya, Zh. Org. Kh., 5 207 (1969); J. Org. Chem., USSR, 5, 200 (1969) describes pyrolysis of ethylene carbonate only with alkali metal halides. It has been surprisingly discovered that the conversion of substituted ethylene carbonates with alkali metal halides produces substituted ethylene epoxides in very high selectivities at high conversion. It is also surprising to note that the particular alkali metal halides discussed in the Shapiro reference act in a very different manner when substituted ethylene carbonates are used instead of the ethylene carbonates used by Shapiro. In fact, many of the catalysts suitable for ethylene oxide formation in Shapiro are inferior for propylene oxide formation from the respective carbonate and vice versa.

Thus, the teachings in Shapiro were of very little use in predicting the activity of substituted ethylene carbonate conversion to substituted ethylene oxide.

SUMMARY OF THE INVENTION

The invention is a process for converting substituted ethylene carbonates to substituted ethylene oxides by heating the carbonates in the presence of a catalyst which is selected from the group of alkali metal halides consisting of lithium fluoride, sodium fluoride, potassium fluoride, sodium chloride and potassium chloride.

DESCRIPTION OF THE PREFERRED EMBODIMENTS

The substituted ethylene carbonates useful in the process of my invention have the general formula

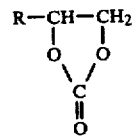

wherein R is alkyl, aryl, substituted alkyl, substituted aryl, alkaryl or aralkyl and preferably wherein R is an alkyl group from 1 to 20 carbon atoms and more preferably from 1 to 7 carbon atoms and still more preferably wherein R is one carbon atom and the substituted ethylene carbonate is propylene carbonate.

The catalysts useful in the process of my invention are the alkali metal halides and lanthanum iodide.

A solvent may or may not be used depending on the catalyst and the carbonate chosen. It has been found useful to dissolve sufficient catalyst for a useful reaction rate, thus, if the carbonate is not a good solvent for the catalyst, a polar aprotic solvent may be used. Useful solvents used in the method of my invention are sulfolane (tetramethylene sulfone). This solvent has been found to be outstanding since it provides good catalyst solubility and has a high boiling point. In any event, the solvent used must be unreactive with both the catalyst and with the substituted ethylene carbonate and also with the reaction product. Examples of some suitable solvents are hydrocarbons, ethers, polyethers, ketones, esters, amides, nitro compounds, sulfoxides, sulfones, tertiary amines, chloro compounds, or any other unreactive compounds. Compounds which are not suitable may be exemplified by alcohols, primary or secondary amines and thiols. Use of a solvent is optional and inclusion is left to the preference of the operator.

The amount of catalyst necessary is dependent upon the particular halide catalyst chosen, and on the rate desired for the reaction to proceed. An excess of catalyst may be used, that is, more than is soluble in the reaction medium. This excess is not necessary, however. The minimum amount of catalyst necessary is a function of the desired rate considered with the temperature to be used for the reaction. The excess of catalyst is often preferred from an operational viewpoint so that the rate which the decomposition occurs may be controlled exclusively by the temperature. Amounts ranging from about 0.01 to 100 weight percent of substituted ethylene carbonate are recommended.

The pyrolysis temperature may range from about 160° C. to about 250° C. or more if greater than atmospheric pressure is employed. The pressure may range from 0.05 atmospheres to about 10 atmospheres. These parameters are cited merely as guidelines and are not intended to limit the scope of the invention.

EXAMPLE I

Batch Reactions

The following experiments in Table I were conducted by charging the substituted ethylene carbonate (200 gm) and catalyst to a glass reactor equipped with a mechanical stirrer, thermometer, 12 inch Vigreux column topped with K-type distillation head and dry ice condenser. The mixture was heated as indicated, the overhead collected and weighed and both overhead and bottoms, if any, analyzed by gas liquid chromatography. Calculations were performed as follows:

$$\text{Conversion} = \frac{\text{wt. of Carbonate Charged} - \text{wt. of Bottoms After Reaction (excluding catalyst)}}{\text{wt. of Carbonate Charged}} \times 100$$

$$\text{Selectivity}^* = \frac{\text{wt. of Overhead} \times \text{G.C. \% Oxide in Overhead} \times 100}{\text{Theoretical Wt. Oxide from Carbonate Charged}} \div \text{Conversion}$$

$$\text{G.C. Selectivity} = \frac{\text{Percent Oxide}^{} \times 100}{\text{Percent Oxide}^{} + \text{Percent By-Products}^{**} \text{ (excluding carbonate and } CO_2\text{)}}$$

*Subject to weighing and handling errors; G.C. Selectivity may be a better indication of the actual overhead composition.

**In overhead, as determined by gas-liquid chromatography

TABLE I

| Run No. | Carbonate | Catalyst (g) | Ovhd. (g) | Time (hr) | Temp. Range °C. | Conversion % | OS* | G.C.S.** |
|---|---|---|---|---|---|---|---|---|
| 1 | 1,2-Butylene | KI(5.0) | 112.5 | 2.7 | 184–200 | 96.5 | 90.5 | 95.8 |
| 2 | 1,2-Propylene | KBr(5.0) | 50.0 | 3.1 | 210–216 | 42.5 | 96.6 | 97.8 |
| 3 | 1,2-Propylene | CsBr(5.0) | 101 | 4.0 | 215–236 | 93.0 | 94.1 | 98.5 |
| 4 | 1,2-Propylene | KCl(0.25) | 38 | 3.0 | 206–208 | 35.1 | 94.0 | 98.7 |
| 5 | 1,2-Propylene | CsI(5.0) | 106 | 2.3 | 219–230 | 97 | 94.3 | 98.1 |
| 6 | 1,2-Propylene | RbI(5.0) | 103 | 1.6 | 218–230 | 94.0 | 95.1 | 98.7 |
| 7 | 1,2-Propylene | CaI2(5.0) | 106 | 1.0 | 198–220 | 93.8 | 71.4 | 71.8 |
| 8 | 1,2-Propylene | KF(1.0) | 34 | 3.0 | 194–198 | 33.0 | 87.6 | 96.7 |
| 9 | 1,2-Propylene | LaI3(1.0) | 70 | 4.0 | 222–237 | 62.5 | 97.0 | 98.5 |
| 10 | 1,2-Propylene | NaCl(1.0) | 32 | 3.0 | 202–210 | 22.0 | 125.1 | 97.8 |
| 11 | 1,2-Propylene | MgI2(0.93) | 101 | 1.5 | 210–211 | 97.1 | 62.6 | 68.4 |
| 12 | 1,2-Butylene[1] | NaCl(5.0) | 29 | 4.0 | 228–234 | 98.0 | 94.5 | 99.0 |

*Oxide Selectivity (%)
**G.C. Selectivity (%)

[1] 50g butylene carbonate was charged instead of the usual 200. Note that the selectivity to butylene oxide was superior with NaCl as catalyst rather than with KI as catalyst. This result is opposite to that found for ethylene carbonate conversion to ethylene oxide, where iodides were more selective than chlorides (See Shapiro above). Note that alkaline earth halides provide poor selectivities to propylene oxide. Also the above shows a very high conversion using potassium fluoride whereas Shapiro et. al. disclosed no epoxide production using fluorides.

EXAMPLE II
Continuous Reactions

A solvent may be used to advantage in a continuous, stirred tank reaction. The examples in Table II illustrate increased selectivity to propylene oxide when a solvent is used.

The batch reaction was conducted by charging both catalyst and propylene carbonate (200 g) to a reactor and distilling off product as it was formed. The continuous reaction was conducted by charging solvent and catalyst to the same reactor and adding propylene carbonate (200 g) to maintain approximately the original liquid level in the reactor.

TABLE II

| Reaction Made | Experiment Number | Catalyst (g) | Reaction Time (hr) | Rxn. Temp. C.° | Overhead Wt. (g) | Carbonate Conver. % | Propylene Oxide Selectivity % | Propylene Oxide in Overhead % |
|---|---|---|---|---|---|---|---|---|
| Batch | 13 | KCl(5.0) | 4.0 | 220–242 | 83 | 89.5 | 55.8** | 68.4 |
| Continuous* | 14 | KCl(5.0) | 5.3 | 237–242 | 106 | 98.0 | 94.6 | 99.4 |

*Solvent = 150g sulfolane
**21.2% Selectivity to allyl alcohol.

Continuous Reactions:

A number of continuous reactions were done to illustrate this technique of operation. A similar apparatus was used in these experiments as was used in the batch reactions described earlier. An addition funnel was added to admit the carbonate dropwise so that the liquid level remained constant at the approximate original level. The data is recorded in Table III for these experiments with propylene carbonate (PC).

TABLE III

| Experiment Number | Solvent (g)** | Carbonate (g) | Catalyst (g) | Time (hr) | Temp. (°C.) | Conversion (%) | Selectivity (%) | G.C. Selectivity (%) |
|---|---|---|---|---|---|---|---|---|
| 15 | — | Propylene(500)* | KI (5) | 4.8 | 186–187 | 98 | 93.4 | 97.7 |
| 16 | — | Propylene(500)* | KBr (5) | 7.5 | 210–225 | 76.6 | 94.6 | 99.3 |
| 17 | Sulfolane | Propylene(200) | NaCl (10) | 4.8 | 234–240 | 86.5 | 96.0 | 99.4 |
| 18 | O—Nitro—Toluene | Propylene(113) | KBr (5) | 6.0 | 220 | 66.4 | 92.1 | 95.6 |
| 19 | Sulfolane | Propylene(200) | NaCl (1.0) | 6.3 | 220–240 | 93.5 | 97.3 | 98.5 |

*Reactor was charged initially with 100g of the total propylene carbonate and the catalyst.
**150g solvent was used where solvent was employed.

A continuous reaction was conducted in an apparatus similar to that used in the previously described continuous reactions for the pyrolysis of glycerine carbonate. The pyrolysis was conducted at a pressure of 15–25 mmHg at 160° to 196° C., continuously removing overhead while adding glycerine carbonate (200g). The initial charge to the reactor was 5g catalyst and 10g glycerine carbonate. The data are recorded in Table IV.

TABLE IV

| Experiment Number | Catalyst | Time (hr) | Conversion (%) | Selectivity (%) to Glycidol | G.C. Selectivity (%) to Glycidol | Pressure (mm Hg) |
|---|---|---|---|---|---|---|
| 20* | NaI | 1.0 | 82.6 | 66.8 | 86.7 | 15–25 |
| 21 | KBr | 4.1 | 86.6 | 70.5 | 88.9 | 15–22 |
| 22 | NaCl | 3.0 | 84.3 | 71.1 | 91.8 | 15 |

*Only 115g glycerine carbonate total was reacted.

EXAMPLE III as small as 0.05 g, the catalyst tends to deactivate with propylene carbonate as a substrate.

TABLE VI

| Expt. No. | Catalyst, wt. | Reagent, 0.5 mole | Reaction temp., °C. | Time | Yield oxide, % | Yield polymer | Comments |
|---|---|---|---|---|---|---|---|
| 26 | NaCl, 0.05g | PrCO$_3$ | 193–201 | 2.0 hr. | 0 | 0 | No rxn. PrCO$_3$ recovered |
| 27 | NaCl, 0.05g | EtCO$_3$ | 189–200 | 2.3 hr. | 25.9 | 74.1* | Oxide 99.0% pure |
| 28 | KCl, 0.06g | PrCO$_3$ | 198–200 | 2.0 | 14.5 | 0 | Oxide 99+% pure |
| 29 | KCl, 0.06g | EtCO$_3$ | 192–201 | 1.9 | 20.0 | 80.0* | Oxide 98.9% pure |

*The polymer was ca. 2000 molecular weight.

The examples in Table V point out the great discrepancies found between the prior art and the process of my invention. For example, alkali metal fluorides are reported by Shapiro above to give no ethylene oxide in the pyrolysis of ethylene carbonate. We have found that these fluorides operate as catalysts in the conversion of propylene carbonates to propylene oxide, however. Selectivities to propylene oxide vary depending on the alkali metal as observed in the table below.

TABLE V (Batch Reactions)

| Fluoride | Expt. No. | Temp. °C. | Conversion % | Overhead Selectivity** Propylene Oxide (%) | Allyl Alcohol % | Yield C$_3$ Products (%) |
|---|---|---|---|---|---|---|
| Lithium | 23 | 232 | 99.7 | 98 | 0* | 32.5 |
| Sodium | 24 | 195–230 | 70.8 | 58 | 41 | 40 |
| Potassium | 25 | 194–198 | 37.6 | 97 | 2.9 | 29.9 |

*2% propionaldehyde constituted the remainder of the overhead
**Percent product comprising the overhead, includes all C$_3$ products produced.

These experiments in Table V were performed by heating 200 g propylene carbonate with 5 g catalyst and collecting the overhead with a dry ice condenser and receiver. Yields are calculated basis propylene oxide expected from the starting weight of proylene carbonate.

EXAMPLE IV

The following experiments (Table VI) demonstrate that under the reaction conditions used by Shapiro et. al. to attempt ethylene oxide production from ethylene carbonate with NaCl and KCl catalysts that the manufacture of propylene oxide from propylene carbonate was very different. Note that while polymer formation was prevalent under the conditions of Shapiro using ethylene carbonate, no polymer was formed under the same conditions using the propylene carbonate .

While no propylene oxide was formed under these conditions using sodium chloride, Tables I and III above demonstrate conversion to propylene oxide under similar conditions. The absence of propylene oxide formation in Experiment No. 26 in contrast to the good yields of Experiment Nos. 10, 17 and 19 can be directly attributed to the low amount of NaCl catalyst used. Experiment No. 26 was run under Shapiro's conditions and therefore, only 0.05 g NaCl was used while 1.0, 10.0 and 1.0 g NaCl was used in Experiment Nos. 10, 17 and 19 respective. When using catalyst amounts

EXAMPLE V

Alkali metal carbonates are reported to be efficient catalysts for the production of substituted olefin oxides from olefin carbonates (O.L.S. No.1,940,205). Selectivities are as high as 96% with carbonate conversions up to 90%. Temperatures of 290° to 340° C. are employed resulting in by-products. These are (from propylene carbonate) acetone, propionaldehyde, and allyl alcohol.

In our invention, lower pyrolysis temperatures are employed in a liquid phase reaction to achieve higher selectivities at substantially quantitative conversions. Generally more allyl alcohol is formed in the process of O.L.S. No. 1,940,205.

Shapiro relates that the highest yield of ethylene oxide from ethylene carbonate is derived by using lithium chloride from among the alkali metal chlorides. We find, however, that all of the alkali metal chlorides are essentially equivalent in the propylene carbonate pyrolysis with lithium chloride one of the poorest. No polymer formation was observed with propylene carbonate as it was with ethylene carbonate in Shapiro.

Lithium iodide is reported in Shapiro as one of the most selective and efficient catalysts for ethylene oxide production from ethylene carbonate. This iodide is the least selective iodide for propylene oxide production from propylene carbonate.

As Table VII shows in similar experiments, LiI produced propylene oxide with a selectivity of only 27.5% whereas, RbI gave 95.1% selectivity, both at 90% conversion of propylene carbonate. Using 5 g catalyst and 200 g propylene carbonate charged to a glass reactor, the mixture was heated and overhead collected with a dry ice condenser.*

*Propylene carbonate was added dropwise to a mixture of the catalyst and 150 g of sulfonate.

TABLE VII

| Expt. No. | Catalyst | Time (hr) | Temp. °C. | Conversion % | % Propylene Oxide Selectivity | % Propylene Oxide in Overhead |
| --- | --- | --- | --- | --- | --- | --- |
| 30 | LiI | 5.0 | 170–185 | 97.5 | 27.5 | 28.2 |
| 31 | RbI | 1.6 | 218–230 | 94.0 | 95.1 | 98.7 |

*Propylene carbonate was added dropwise to a mixture of the catalyst and 150g of sulfolane.

We claim:

1. A process for the preparation of a substituted ethylene epoxide of the formula

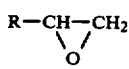

wherein R is alkyl, aryl, substituted alkyl or substituted aryl which comprises heating the corresponding substituted ethylene carbonate having the formula

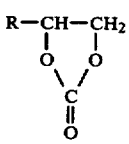

wherein R is defined as above in the presence of a catalytic amount of a catalyst which is selected from the group of alkali metal fluorides consisting of lithium fluoride, sodium fluoride, and potassium fluoride.

2. The process of claim 1 wherein the substituted ethylene carbonate is heated in the presence of said catalyst at a temperature in the range of from 150° to 300° C. and a pressure ranging from about 0.05 to 10 atmospheres.

3. The process of claim 1 wherein said catalyst is present in an amount ranging from about 0.1 to 100 weight percent of the substituted ethylene carbonate.

4. A process for the preparation of propylene oxide which comprises heating propylene carbonate in the presence of a catalytic amount of a catalyst which is selected from the group of alkali metal fluorides consisting of lithium fluoride, sodium fluoride, and potassium fluoride.

5. A process for the preparation of a substituted ethylene epoxide of the formula $$R-CH-CH_2$$
$$\diagdown \diagup$$
$$O$$

wherein R is alkyl, aryl, substituted alkyl or substituted aryl which comprises heating the corresponding substituted ethylene carbonate having the formula $$R-CH-CH_2$$
$$| \quad |$$
$$O \quad O$$
$$\diagdown \diagup$$
$$C$$
$$\|$$
$$O$$

wherein R is defined as above in the presence of a catalytic amount of a catalyst comprising an alkali metal fluoride.

6. A process for the preparation of propylene oxide which comprises heating propylene carbonate in the presence of a catalytic amount of a catalyst comprising an alkali metal fluoride.

* * * * *